United States Patent
Sabsabi et al.

[19]

[11] Patent Number: 6,008,896
[45] Date of Patent: Dec. 28, 1999

[54] METHOD AND APPARATUS FOR SPECTROSCOPIC ANALYSIS OF HETEROGENEOUS MATERIALS

[75] Inventors: Mohamad Sabsabi, Boucherville; Paolo Cielo, Montreal, both of Canada

[73] Assignee: National Research Council of Canada, Ottawa, Canada

[21] Appl. No.: 09/108,210

[22] Filed: Jul. 1, 1998

[51] Int. Cl.⁶ .................................................. G01N 21/63
[52] U.S. Cl. ............................................................ 356/318
[58] Field of Search ....................................... 356/317, 318

[56] References Cited

U.S. PATENT DOCUMENTS

| | | | |
|---|---|---|---|
| 3,901,599 | 8/1975 | Meric | 356/318 |
| 4,645,342 | 2/1987 | Tanimoto et al. | 356/318 |
| 4,986,658 | 1/1991 | Kim | 356/318 |
| 4,995,723 | 2/1991 | Carlhoff et al. | 356/318 |
| 5,042,947 | 8/1991 | Pötzchke et al. | 356/318 |
| 5,379,103 | 1/1995 | Zigler | 356/318 |

OTHER PUBLICATIONS

Correction of Matrix Effects in Quantitative . . . Journal of Analytical Atomic Spectrometry Feb. 97 vol. 12 (1983–188).

*Primary Examiner*—F. L. Evans
*Attorney, Agent, or Firm*—Juliusz Szereszewski

[57] ABSTRACT

A method and apparatus for rapid in-situ spectroscopic analysis of unknown heterogeneous materials is disclosed. The apparatus uses a high power pulsed laser whose beam is focused on the material, typically a porous compound of unknown composition such as an amalgamated powder or a mineral sample. The pulsed laser beam vaporizes a small volume of the material and produces a plasma having an elemental composition which is representative of the material composition. The optical emission of the plasma is analyzed with an optical spectrometer. The pulsed spectrum is detected by a gated photodiode array detector or by an array of individually positioned photomultipliers, to detect a background emission and a line emission representative of a given element present in the material. Because such measurements may fluctuate considerably for porous materials due to unpredictable variations of the plasma temperature and the amount of vaporized mass, the signals are normalized by establishing a ratio of the intensity of the signals to that of the background plasma emission.

13 Claims, 4 Drawing Sheets

METHOD AND APPARATUS FOR SPECTROSCOPIC ANALYSIS OF HETEROGENEOUS MATERIALS

BACKGROUND OF THE INVENTION

1. Field of the Invention

This invention relates to a transient, rapid spectroscopic method for analysis of heterogeneous materials such as porous compounds of unknown composition, amalgamated powders or mineral samples.

2. Related Art

Most analytical techniques used in industry require taking samples to the laboratory, to be analyzed by time consuming procedures involving instrumentation such as Auger and mass spectrometers, EDS, liquid or gas chromatography, graphite furnace atomic absorption spectroscopy or inductively coupled plasma optical emission spectrometry. Faster in-situ methods such as spark-discharge optical spectrometry are only applicable to electrically conductive materials, while X-ray backscattering probes are limited in sensitivity.

An emerging method, laser induced plasma spectroscopy, promises to provide rapid, in-situ compositional analysis of a variety of materials in hostile environments and at a distance. Basically, this method includes focusing a high power pulsed laser on the material, thus vaporizing and ionizing a small volume of the material to produce a plasma having an elemental composition which is representative of the material composition. The optical emission of the plasma is analyzed with an optical spectrometer to obtain its atomic composition. This method has been applied to a variety of materials and industrial environments, as exemplified in the following documents.

U.S. Pat. No. 4,645,342 by Tanimoto et al. describes a probe for spectroscopic analysis of steel including focusing an infrared laser pulse on the steel material and collecting, at an angle of 16 degrees or more, the light emitted by the irradiated surface spot. The light is spectrally analyzed after a firstly emitted light (white noise) is excluded. The spectral background of the individual emissions is subtracted to obtain the net intensity of preset spectral lines representative of given elements, and the intensity of said spectral lines is related to the concentration of said elements in the steel material. The analyzed material, massive steel, has a good homogeneity. This cannot be said of heterogeneous materials such as porous materials where particle-to-particle interfaces represent randomly distributed thermal barriers which may considerably affect the plasma temperature and the amount of vaporized mass.

U.S. Pat. No. 4,986,658 to Kim describes a probe for molten metal analysis by laser induced plasma spectroscopy. The probe contains a high-power laser producing a pulse having a triangular pulse waveshape. When the probe head is immersed in the molten metal, the pulsed laser beam vaporizes a portion of the molten metal to produce a plasma having an elemental composition representative of the molten metal composition. Within the probe, there is provided a pair of spectrographs each having a diffraction grating coupled to a gated intensified photodiode array. The spectroscopic atomic emission of the plasma is analyzed and detected for two separate time windows during the life of the plasma using two spectrometers in parallel. The first time window analyzes the plasma plume before it reaches thermal equilibrium shortly after the termination of the laser pulse, typically 10 ns long, to detect line reversals, as caused by absorption of radiation emitted by the hotter inner portion of the plasma plume by relatively cooler outer portions of the plasma plume. Thereafter, after the plasma has reached thermal equilibrium, typically after 1 µs, a second time window analyzes the more conventional line emissions from the optically emissive plasma. The spectra obtained during either the first or the second time window, or a combination of both, can be used to infer the atomic composition of the molten metal. Because the metal is molten, it has a good homogeneity. Again, this cannot be said for heterogeneous materials such as porous materials where particle-to-particle interfaces represent randomly distributed thermal barriers which may considerably affect the plasma temperature and the amount of vaporized mass.

U.S. Pat. No. 4,995,723 by Carlhoff et al. describes a similar probe for liquid metal analysis in a melting vessel. In this case, the pulsed laser beam and the fiber optic collector for the spectrometer are pointed to the liquid metal through a lateral opening in the vessel, through which opening a hot, inert gas is continuously injected to provide a clean and oxide-free molten metal surface to be analyzed by laser induced plasma spectroscopy. Again, the material is here homogeneous.

U.S. Pat. No. 5,042,947 by Pötzschke et al. describes an application of laser induced plasma spectroscopy for the sorting of solid metal particles, namely shredder scrap from automotive recycling processes. Multiple laser pulses are here used to clean the surface from impurities, and up to 30 particles per second can thus be sorted depending on the resulting composition, typically aluminium, zinc, copper, lead and steel. Because here the purpose is sorting rather than precise compositional analysis, a relatively low precision and sensitivity can be accepted in this case.

Zigler in U.S. Pat. No. 5,379,103 describes a mobile laboratory for in-situ detection of organic and heavy metal pollutants in ground water. Pulsed laser energy is delivered via fiber optic media to create a laser spark on a remotely located analysis sample. The system operates in two modes, one being based on laser induced plasma spectroscopy and the other on laser induced fluorescence. In the first operational mode, the laser beam guided by optical fiber is focused by a lens on the sample to generate a plasma. The emitted spectrum is analyzed and used to detect heavy metals. In the second mode the focusing laser energy is removed allowing the laser beam via fiber optic to irradiate the sample, so that organic molecules with an aromatic structure emit absorbed ultraviolet energy as fluorescence. The emitted fluorescence light is transmitted via fiber optic media for further analysis. The measured wavelength and time characteristics of the emitted fluorescence can be compared against predetermined characteristics to identify the organic substances in the analysis sample. Zigler et al analyze trace quantities of both molecules and atoms in ground water. In the case of molecules, molecular spectra are analyzed using fluorescence. Again, the probed material, ground water, is homogeneous and compact, while the analysis of heterogeneous or porous materials must face signal variabilities requiring special techniques for improving their reliability, as described in the present disclosure.

The variability of the line emission signal detected in laser induced plasma spectroscopy originates from the fact that the intensity of the emission line of a given element i present in the plasma can be written as (see the paper by Chaléard et al., "Correction of matrix effects in quantitative elemental analysis with laser ablation optical emission spectrometry", Journal of Analytical Atomic Spectrometry, vol. 12, pp. 183–188, Febuary 1997):

$$I(i) = KC(i)Me^{-E/k}$$

where K is a constant which takes into account the collection efficiency of the apparatus, C(i) is the concentration of element i in the plasma, which is the unknown to be measured, M is the mass of matter vaporized in the plasma plume, E is the atomic energy level to which the atom has to be raised in the plasma in order to provide, by de-excitation, the emitted intensity, k is Boltzmann's constant, and T is the average temperature of the plasma. E and k are known constants, while K can be established by calibration, so that in order to evaluate C(i) from a measurement of the emitted intensity I(i), the values of T and M need to be determined.

The analysis of heterogeneous and porous materials poses certain problems due to the random variability of the surface orientation in the small area (typically less than 1 mm in diameter), where the laser pulse happens to strike the surface, as well as to the possible presence of subsurface thermal barriers due to particle-to-particle interfaces which cool down the plasma by an amount unpredictable from shot to shot due to the correspondingly erratic local thermal conductivity of the material under the irradiated surface. Because of the above factors, neither T nor M are repetitive enough to be evaluated once and for all in the calibration stage, but may vary unpredictably from shot to shot or from one material to another. Methods for evaluating these two variables at each laser shot are thus required if this technique is to provide the required reliability.

The above mentioned paper by Chaléard et al provides an answer to these requirements. The temperature T of the plasma can be evaluated by the well known technique of establishing the ratio of two emission lines having different excitation energy levels and applying Boltzmann's law (see the above-mentioned paper at p. 186). As to the evaluation of the mass M of the matter vaporized in the plasma plume, it is estimated by using a microphone to detect the acoustic pulse produced by the expanding plasma induced by the laser shot. For flat metallic samples and under controlled laboratory conditions, it was demonstrated that the acoustic signal varied linearly, albeit with a small slope, with the amount of the mass ablated by the laser shot, such that by establishing a ratio of the detected intensity to the intensity of the acoustic signal, the normalized signal thus obtained was relatively independent of variations of the laser irradiance.

However, the utilization of an acoustic sensor for signal normalization has a number of drawbacks, particularly in the analysis of non-flat or porous materials:

a separate microphone is required to be positioned close to the irradiated sample, complicating the probe setup. The acoustic signal (differently from the optical emission signal which is collected by imaging the spectrometer slit, typically 0.1 mm wide, across the plasma which is viewed as a disk of typically 1 mm in diameter) varies as $d^{-2}$, where d is the distance from the acoustic sensor to the irradiated spot. Consequently, the acoustic signal varies with the surface position, making it difficult to maintain signal repetitivity when scanning convoluted surfaces. Furthermore, the acoustic signal is typically affected by spurious reflections of the acoustic wave on an irregular sample surface or on nearby objects, while its intensity may be affected by possible variations of the air absorptivity due to variations in temperature, humidity etc;

the acoustic pulse, due to the relatively large wavelength of the sound detectable by such microphones, integrates spatially and temporally across the full plasma plume and for the full duration of the plasma discharge.

Consequently, the acoustic signal may be affected by spatial fluctuations of the random plasma plume outside the typically 0.1 mm wide slice of the plume which is imaged by the spectrometer. For this reason, in the above mentioned work (see the paper by Chaléard et al. at p. 184) a spatial filter was introduced in the laser beam to insure a flattened, "top hat" distribution. This severely reduces the useful laser power, while not assuring signal repetitivity in case of laser-to-spectrometer misalignment. Similarly, the acoustic signal integrates over the full, typically a few tens of $\mu s$, duration of the plasma, while the detectors are gated to optimally respond only to a portion of this duration, within which portion the emission intensity may vary independently of the overall integrated plasma intensity.

The object of the present invention is to provide a method and apparatus for a reliable analysis of heterogeneous materials by laser induced plasma spectroscopy using a signal normalization which requires no physically separate sensor, so that both the signal and the normalizing factor are affected in an identical manner when scanning convoluted or irregular surfaces, or in the presence of fumes or other limitations to air transparency, while no unwanted spatial or temporal integration effects will take place.

SUMMARY OF THE INVENTION

Accordingly, one object of this invention is to provide a new method and apparatus for in-situ transient spectroscopic analysis of unknown heterogeneous materials such as porous compounds of unknown composition, amalgamated powders or mineral samples, which is free of the problems of the prior art and which provides an accurate and reproducible indication of the concentration of the selected elements during a short time in the order of seconds. It is a further object of this invention to provide a method as defined above which is reliable and repetitive in a wide variety of industrial or hostile environments.

These and other objects are achieved according to the invention by providing a new method and apparatus for in-situ transient spectroscopy analysis of unknown materials. The invention uses powerful laser pulses to irradiate a representative quantity of a heterogeneous sample and form a microplasma or spark. As a result of the high temperature plasma generated, a small amount of the material is vaporized and ionized, molecules are dissociated, and atoms and ions are in excited states, thus allowing emitting species in the plasma to be identified by spectrally and temporally resolving the spark light. Immediately after the laser pulse, the plasma emission consists of an intense continuum and emitted light consisting initially of very broad lines due to high electron density. Typically, 1 $\mu s$ after the laser pulse, the continuum decreases significantly, the lines are narrower and well resolved, and the signal-to-noise ratio is improved. Under these conditions, the atomization is complete and the plasma is close to local thermal equilibrium and is favorable for spectrochemical analysis. The radiation emitted by the laser induced plasma is then collected using an optical gating system, by a lens and guided by an optical fiber to a spectrometer. The spectrometer is equipped with a diffracting grating coupled to a gated, intensified photodiode array detector or other means to detect simultaneously and during a specified time, the specific element lines for several elements found in the analyzed material, while the continuum plasma emission is used to normalize the line emission signal.

BRIEF DESCRIPTION OF THE DRAWINGS

These and other objects, features and advantages of the present invention will become apparent from a consideration of the following detailed description of the invention in conjuction with the drawings in which.

DETAILED DESCRIPTION OF THE PREFERRED EMBODIMENTS

The method and apparatus of this invention use powerful laser pulses to irradiate heterogeneous materials and form a microplasma or spark on their surfaces. As a result of the high temperature plasma generated, a small amount of the material is vaporized and ionized, its atoms and ions being in excited states, thus allowing emitting species in the plasma to be identified by spectrally and temporally resolving the spark light emission.

Figure 1:
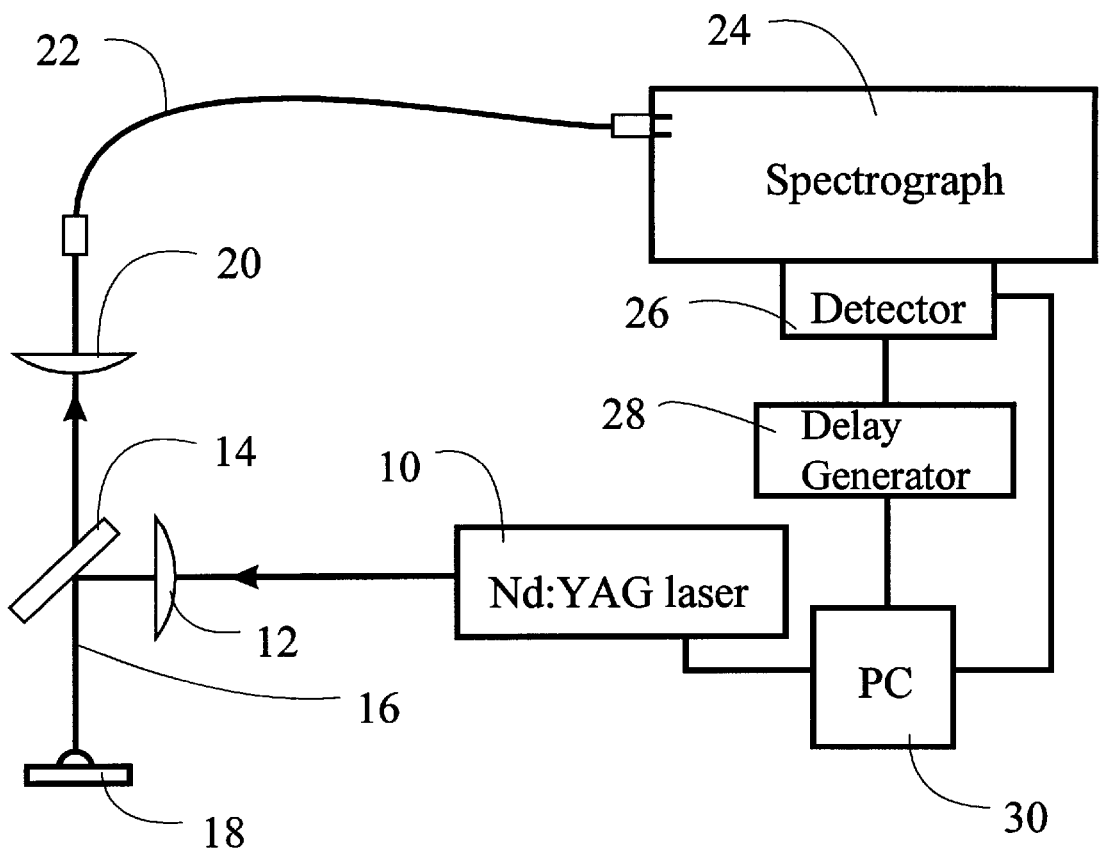
FIG. 1 is an overall block diagram of the apparatus.

FIG. 1 shows a schematic diagram of the apparatus which is the object of the invention. A Nd-YAG (or other suitable high-power pulsed) laser 10 is disposed so as to deliver energy pulses through a lens 12 and a dichroic mirror 14 through an optical path or an optional optical fiber 16 to a sample 18 to generate a plasma. The light emitted by the plasma is collected by an optical system consisting of a lens 20 and an optional optical fiber 22, to the entrance of an optical spectrometer 24 where it is detected in the focal plane by means of an optical multichannel analyzer with high time resolution (on the µs scale). Time resolution of the emitted light is used to reduce interferences and background.

The spectrometer is equipped with a diffraction grating coupled to a gated, intensified photodiode array detector 26, or other detector such as an array of photomultipliers each individually positioned in the focal plane, to detect simultaneously and during a specified time period, a number of emission lines representative of different elements in the material to be analyzed. A delay generator 28 is installed in the system for gating off the unwanted time period such as the early stage of the plasma formation. A fast computer 30 evaluates the measured spectra and calculates the element concentrations via calibration procedures.

Figure 2:
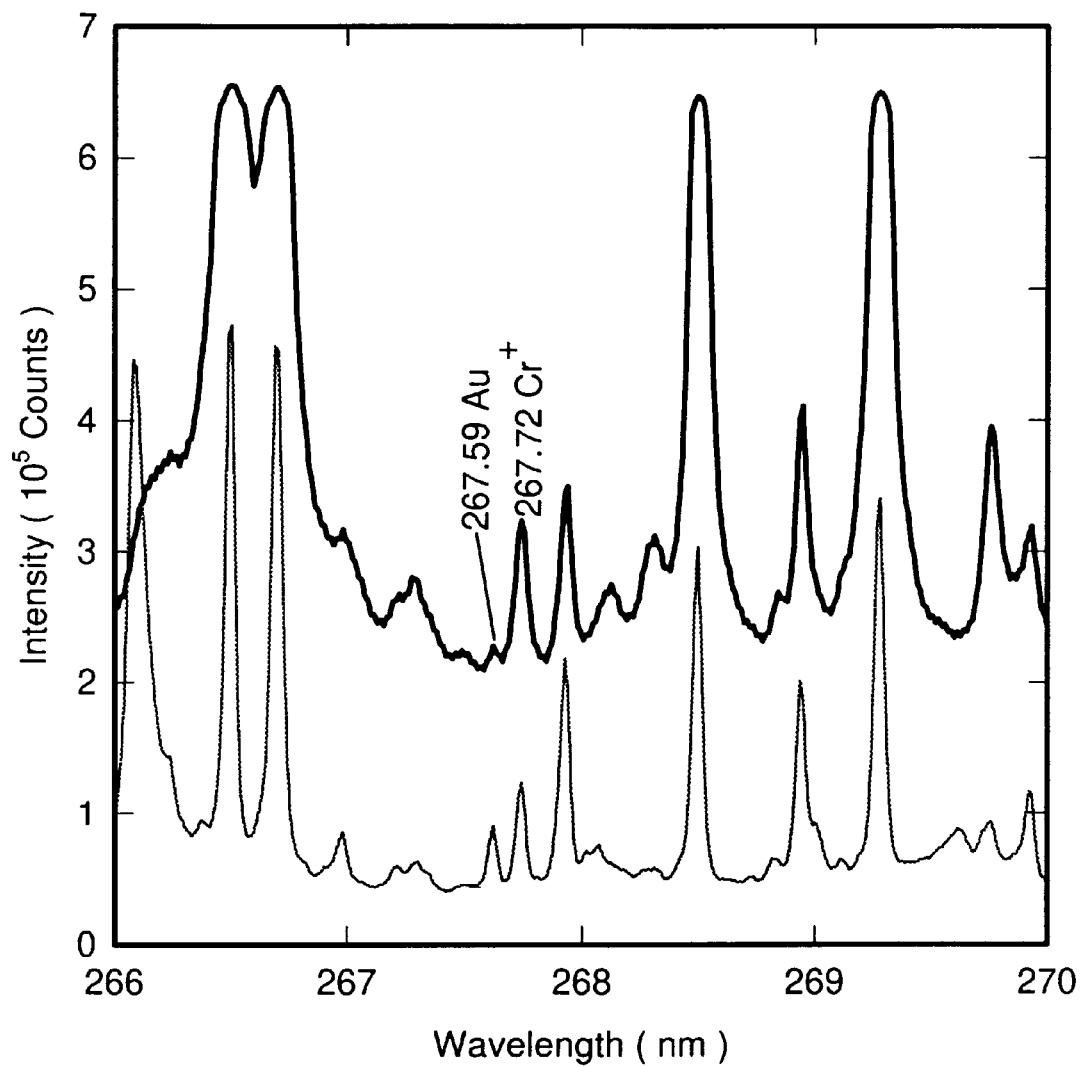
FIG. 2 shows an optical spectrum emission obtained with a Nd-YAG Q-switched laser (energy 180 mJ) focused on a rock sample to produce the plasma, the upper spectrum collected starting at 0.1 µs after the laser pulse and the lower spectrum after 1 µs.

An example of two spectra obtained with such an apparatus after firing a laser pulse on a rock sample containing a small amount (31 ppm) of native gold is shown in FIG. 2. The upper spectrum is obtained after a delay of 0.1 µs from the laser pulse, while the lower curve is obtained after a delay of 1 µs. Line emissions such as the 267.59 nm Au line, which correspond to the difference between two energy levels of a given atom, and thus are characteristic of such an atom, are seen with a better sharpness in the lower spectrum. It is the relative intensity of such lines which gives us the sought information on the concentration of the corresponding species of atoms. These lines are superposed over a relatively featureless background radiation which is called "continuum" and which is subtracted from the line maximum to obtain the net amount of the line emission, as taught by U.S. Pat. No. 4,645,342 by Tanimoto et al. col 8, lines 6 to 8. For the particular Au line, the continuum C (measured at the base of the Au peak) is subtracted from the intensity H of the Au emission line. This continuum is particularly strong in the initial life of the plasma, as shown in the upper spectrum in FIG. 2. Such a continuum is thus normally considered a nuisance, and this explains why typically the detector array is gated so as to record the emission only after a delay of a few µs, when the amplitude of the continuum has considerably decreased. An added advantage of this delay is that the emission lines become narrower, and thus easier to resolve, after the plasma has cooled down.

A number of physical phenomena take place when the laser pulse is fired on the sample. These phenomena must now be briefly summarized in order to better understand the procedure which will be described below. When the power density of the pulsed laser exceeds the breakdown threshold of the material present in the focal volume, the material is rapidly vaporized and a plasma is formed, with high temperatures and electron density. In such a medium, molecules are dissociated, excited and ionized, atoms and ions are present in excited states. The initially transparent matter present in the focal volume becomes optically opaque, absorbing the laser beam. Free electrons in this first period continuously collide with other particles thus releasing what is called the "continuum" radiation, consisting of photons whose energy corresponds to the difference between the kinetic energy of the free electron and the energy of the electron after collision. Because the initial energy of the free electrons has a continuous distribution of possible values, the energy distribution of these photons is continuously distributed over a wide range. Photons are quanta of light whose frequency (which is inversely proportional to their wavelength) is proportional to their energy. Consequently, continuum photons which make up an important part of the initial, hot plasma, produce a continuously distributed, lineless spectrum, which is what we call the continuum, or equivalently, background spectral emission, or white noise as in U.S. Pat. No. 4,645,342. Furthermore, in this initial period after the laser pulse, the plasma is hot and the electron density is high. This results in wider emission lines, whose width is proportional to the electron density due to a physical phenomenon called the "Stark effect". All of this explains why in the initial life of the plasma, as exemplified by the upper curve of FIG. 2, the lines are very broad and the continuum is very strong.

After a few µs from the laser pulse, temperature and electron density drop very quickly, recombination and de-excitation events begin to prevail and the plasma material returns to ground state atomic level thereby emitting light photons of well-specified wavelength. The kinetics during this period can be described as a state of quasi equilibrium and there are relatively small temperature changes observed over a microsecond time scale (see M. Sabsabi and P. Cielo, Appl. Spectrosc., vol. 49, p. 499, 1995). This plasma lifetime is favorable for spectrochemical analysis. By gating off the earlier part of the plasma, one can improve the signal-to-noise ratio, the lines are narrow and well resolved. The plasma generated produces a radiation which is characteristic of the elements contained in the sample and which is supplied to the spectrometer.

The above-mentioned equation (1) is useful to quantitatively relate the intensity of a given emission line, such as the 267.59 nm Au line in FIG. 2, with the element concentration in the plasma and thus in the sample. However, as explained above, with heterogeneous and porous materials this is complicated by the fact that both the plasma temperature and the mass of matter vaporized in the plasma plume may vary unpredictably thus making the analysis unreliable. As mentioned in the Chaléard et al, paper, supra, one can evaluate the plasma temperature by the well-known technique of determining the ratio of two emission lines having different excitation energy levels and applying Boltzmann's law. However, for the reasons explained above the plasma cannot be reliably evaluated by the separate acoustic sensor described in the above paper. A different procedure has thus been provided by the instant invention, as described below.

The conventional approach to infer the element concentration from a spectral analysis as shown in FIG. 2 is to choose a corresponding emission line, such as the 267.59 nm Au line which is more clearly visible in the bottom curve of FIG. 2, measure the amplitude of such line above the background (H-C), and relate such an amplitude to the concentration of the element, in this case 31 ppm as measured independently by established laboratory methods. Passing then to samples with different concentrations of the element sought, one can thus establish a calibration curve which can be later applied to unknown samples.

As mentioned above, however, unpredictable variations in the plasma mass and temperature may introduce random errors when analyzing heterogeneous materials.

Figure 3A:
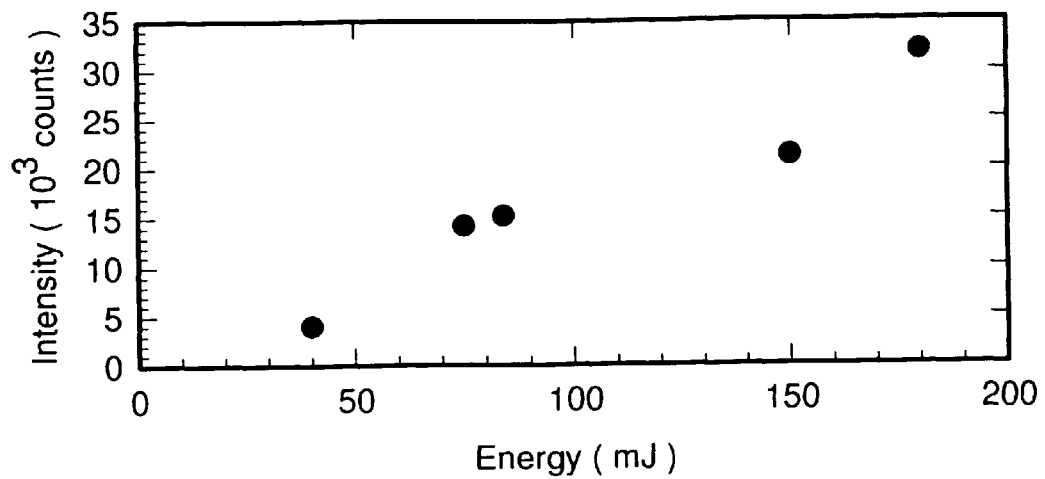
FIG. 3a is a graph showing signal intensities of the Au line (267.59 nm) obtained for a gold-containing sample with laser pulses of varying energy.
Figure 3B:
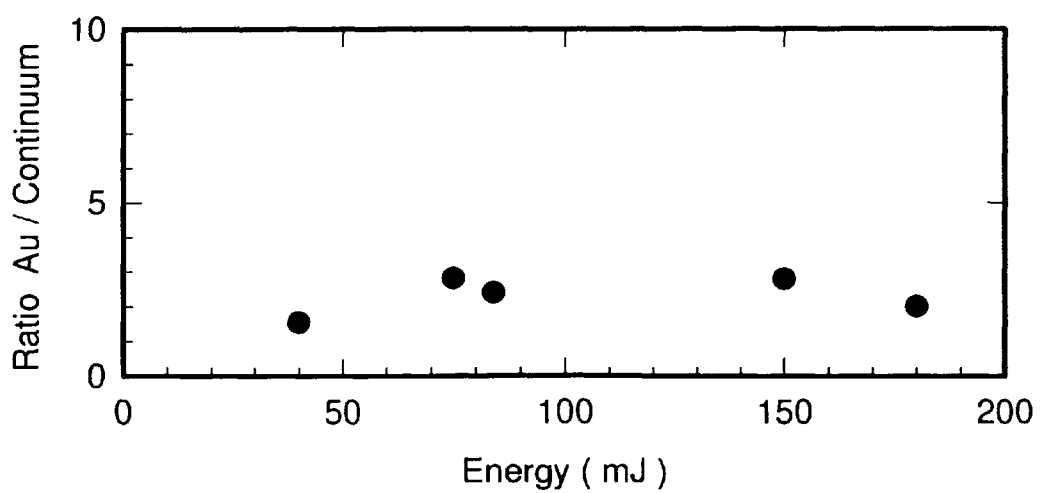
FIG. 3b is a graph showing normalized signals of FIG. 3a obtained according to the invention, plotted against the laser pulse energy.

This is illustrated in FIGS. 3a and 3b. In the FIG. 3a, the intensity of the 267.59 nm Au line is plotted as measured in a sample containing 119 ppm of gold, with laser pulses of different energies. It can be seen that the measured intensity changes by a factor of more than 8 when the pulse energy changes from 40 to 180 mJ. This is because both the plasma mass and temperature increase substantially when the pulse energy is increased, thus providing an unreliable intensity measurement. Indeed, the intrinsic laser pulse energy may change from shot to shot, while the energy density of a given laser pulse may change depending on the local slope of the surface of a convoluted material. Also, the subsurface thermal conductivity may change unpredictably in heterogeneous materials thus affecting the plasma properties, etc, as explained above. Without an adequate normalization method, the intensity may thus vary randomly resulting in an unreliable measurement.

The method to normalize the signal according to the present invention, rather than using a separate acoustic sensor as in the above paper by Chaléard et al, makes use of the recorded continuum. As illustrated in FIG. 3a, the intensity of the 267.59 nm Au line is normalized by establishing a ratio (H-C)/C where H-C is the net intensity (peak height) of the gold emission line and C is the continuum recorded in the region of 267.4 nm, always in the lower graph of FIG. 2. The net intensity H-C can also be termed "net elemental radiation" of a specific line emission for a selected element.

Such a ratio is now plotted in the bottom graph of FIG. 3 for the same laser energy variation as in the upper graph. It can be seen that the signal excursions are much reduced, even without separately evaluating the temperature by the Boltzmann procedure described above.

Figure 4:
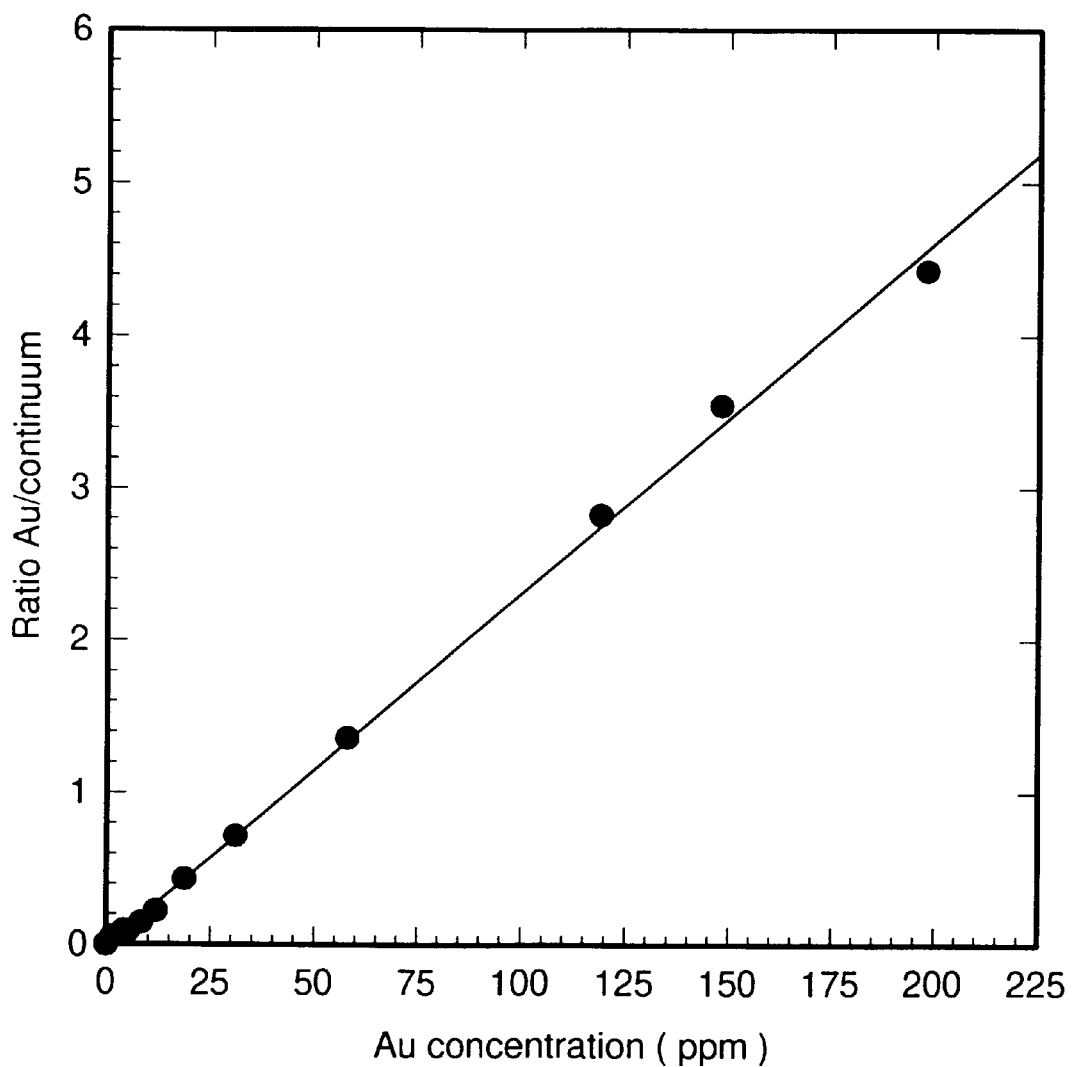
FIG. 4 shows a correlation between the signals obtained according to the invention and the actual concentration of gold measured in the laboratory by a conventional standard analysis.

One can now proceed by recording the gold/continuum (H-C)/C ratios for samples of different gold concentration. Results of actual tests conducted to validate the invention are shown in FIG. 4 that represents a nearly linear calibration curve. The curve can be used to infer the gold concentration in unknown samples from a measurement of the gold line emission intensity and the continuum, and thus independently of the laser energy density or of the local departure from flatness of the sample surface or of the local thermal conductivity distribution below the laser irradiated spot in heterogeneous or porous materials.

While the calibration as illustrated and described above appears to be of satisfactory accuracy, additional rectification is possible by evaluating the plasma temperature using the Boltzmann procedure in conjunction with the Chaléard et al. equation.

It will be understood that the ratio (H-C)/C can be replaced, for the purposes of the invention, with the reverse ratio, C/(H-C), with a similar result.

It should be stressed that the normalization process described above is realized without introducing physically separate sensors such as the acoustic sensor described in the above paper by Chaléard et al. Consequently, variations of the recorded line emission signal as produced by variations in the operation distance when scanning convoluted materials, or by fumes or other limitations to the air transparency, or by particles or other deposits on the lenses, etc., will affect in an equal manner the line emission signal and the recorded continuum, so that their ratio should provide a relatively reliable measurement.

The examples shown in FIGS. 2 to 4 have been provided by using a gated, enhanced photodiode array as the sensor. Similar results could be obtained by using an array of photomultipliers each individually positioned to detect the appropriate line emissions for one or several sought elements as well as the continuum signal. In such case, however, each photomultiplier is individually time gated, so that, if preferred, one can choose different time gating periods for the line intensity signals and for the continuum, while in the case of a photodiode array, the full spectrum including the lines and the continuum is obtained in a single shot during the same time period. Consequently, a different embodiment of the apparatus and method of the invention may consist, in the case where an array of individual photomultipliers is used as detector, of time gating the continuum-recording photomultiplier so as to record its signal in a time period different from the time of the other ones. As an example, the emission lines could be recorded after 1 $\mu$s for best line visibility, while the continuum could be recorded after only 0.1 $\mu$s when the continuum amplitude is higher as shown in the upper trace of FIG. 2, and thus less affected by the electronic noise.

In another variant of the invention, one can record a full spectrum using a photodiode array as shown in FIG. 2, and subsequently use different portions of the recorded spectrum to further optimize the signal information and reliability. As an example, one could take the ratio of two emission lines of a given element having different excitation energy levels and apply the well known Boltzmann's law, as mentioned above and described in the paper by Chaléard et al, to evaluate the temperature of the plasma. Similar well known methods for temperature evaluation include taking the ratio of an ionic and an atomic emission of a given element. One could also record the presence of elements unimportant to the analysis but affecting the level of the continuum, such as iron which has a large number of lines which may affect the continuum level at short time delays after the laser pulse when they are relatively wide and overlap, in order to correct the continuum level by an amount proportional to the presence of iron in the unknown material.

Still another alternative of the method of the invention would be to integrate the full spectrum such as the one shown in the upper trace of FIG. 2 and use this as the continuum, including the presence of emission lines whose area is small compared to the integrated area of the relatively constant background continuum, and whose value is unaffected by the shape of the emission lines. This could be performed either by integrating the signal of the photodiode array, or by diverting part of the unfiltered light with a beam splitter to a detector situated within the spectrometer before the grating.

The above description of the present invention is susceptible to various modifications, changes and adaptations, and the same are intended to be comprehended within the meaning of the appended claims.

We claim:

1. A method for in-situ analysis of an unknown heterogeneous material, the method comprising:

emitting laser pulses from a laser energy emitter, focusing said pulses on a sample of said heterogeneous material to generate a plasma emitting a broad continuum radiation as well as elemental radiation derived from a separate compositional element or elements of said heterogeneous material, measuring both the continuum radiation and a net elemental radiation of a specific line emission which is representative of a selected element present in said heterogeneous material, obtaining at least one normalized signal by establishing a ratio of said net elemental radiation of a specific line emission, and the continuum radiation, and determining the concentration of said element as a function of said at least one normalized signal.

2. The method of claim 1 wherein said concentration is determined from a calibration curve obtained by plotting a number of said normalized signals corresponding to samples with different elemental concentrations against the corresponding concentrations as independently measured.

3. The method of claim 1 wherein said radiation intensity of a specific line emission is measured at a time slot which corresponds to a substantially complete atomization of the plasma.

4. The method of claim 3 where both said continuum radiation and said specific line emissions are measured at a time slot which corresponds to a substantially complete atomization of the plasma.

5. The method of claim 1 where both said continuum radiation and said specific line emissions are measured using an array of individually positioned photomultipliers.

6. The method of claim 4 where both said continuum radiation and said specific line emissions are measured during the same time period after the laser pulse.

7. The method of claim 1 where said continuum radiation is measured during a different time slot than the radiation of said specific line emission.

8. The method of claim 1 where said continuum radiation is measured by integrating the full spectrum including the continuum background as well as the line emissions.

9. The method of claim 1 where said continuum radiation is combined with other lines representative of elements whose concentration affects the continuum level.

10. An apparatus for in-situ spectroscopic analysis of an unknown heterogeneous material, the apparatus comprising:

a laser energy emitter, means for focusing energy emitted from said laser emitter on a sample of said heterogeneous material, thereby generating a plasma emitting a broad continuum radiation as well as elemental radiation derived from separate compositional elements of said heterogeneous material, detecting means for detecting said continuum radiation and for detecting said elemental radiation, analyzing means for spectrally and temporally analyzing said continuum radiation as well as said elemental radiation, processing means for obtaining normalized signals by establishing a ratio of said elemental radiation of specific line emissions which are representative of selected elements present in said heterogeneous material and the continuum radiation, and delay means for gating off a phase in plasma development wherein atomization of said plasma is not substantially complete.

11. The apparatus according to claim 10 comprising separate delay means for detecting said continuum radiation and separate delay means for detecting said elemental radiation derived from separate compositional elements of said heterogeneous material.

12. The apparatus according to claim 10 wherein said detecting means is a gated photodiode array of detectors.

13. The apparatus according to claim 10 wherein said detecting means is an array of individual photomultipliers.

* * * * *